United States Patent [19]

Ederati et al.

[11] Patent Number: 4,636,206

[45] Date of Patent: Jan. 13, 1987

[54] UROSTOMY GUARD

[76] Inventors: Richard M. Ederati, 92 Rickard Dr., East, Oswego, Ill. 60543; Henry J. Perez, 353 Sunset Ave., Aurora, Ill. 60506

[21] Appl. No.: 749,462

[22] Filed: Jun. 27, 1985

[51] Int. Cl.[4] .............................................. A61F 5/44
[52] U.S. Cl. .................................................. 604/340
[58] Field of Search ............................... 604/332–345, 604/277, 339–342

[56] References Cited

U.S. PATENT DOCUMENTS 2,656,838  10/1953  McConnell .......................... 604/342
3,398,744   8/1968  Hooper ................................ 604/340
3,713,445   1/1973  Marsan ................................ 604/336

FOREIGN PATENT DOCUMENTS 2094154  9/1982  United Kingdom ................. 604/345

*Primary Examiner*—C. Fred Rosenbaum
*Assistant Examiner*—J. L. Kruter
*Attorney, Agent, or Firm*—Edmond T. Patnaude

[57] ABSTRACT

A guard for use in cooperation with an adhesively-secured ostomy pouch has a generally kidney-shaped configuration with a concave inner surface. The guard is positionable over the connection between the ostomy patient and is adapted to be secured against the abdomen of the ostomy patient without restricting fluid discharges into the pouch. An upper edge of the guard provides a seal with the abdomen for protecting the adhesive connection of the pouch as the patient is shower bathing. The kidney-shape of the guard allows the pouch to exit from beneath the guard and also permits the patient to comfortably assume either a sitting or standing position while the seal between the guard and abdomen is maintained.

6 Claims, 5 Drawing Figures

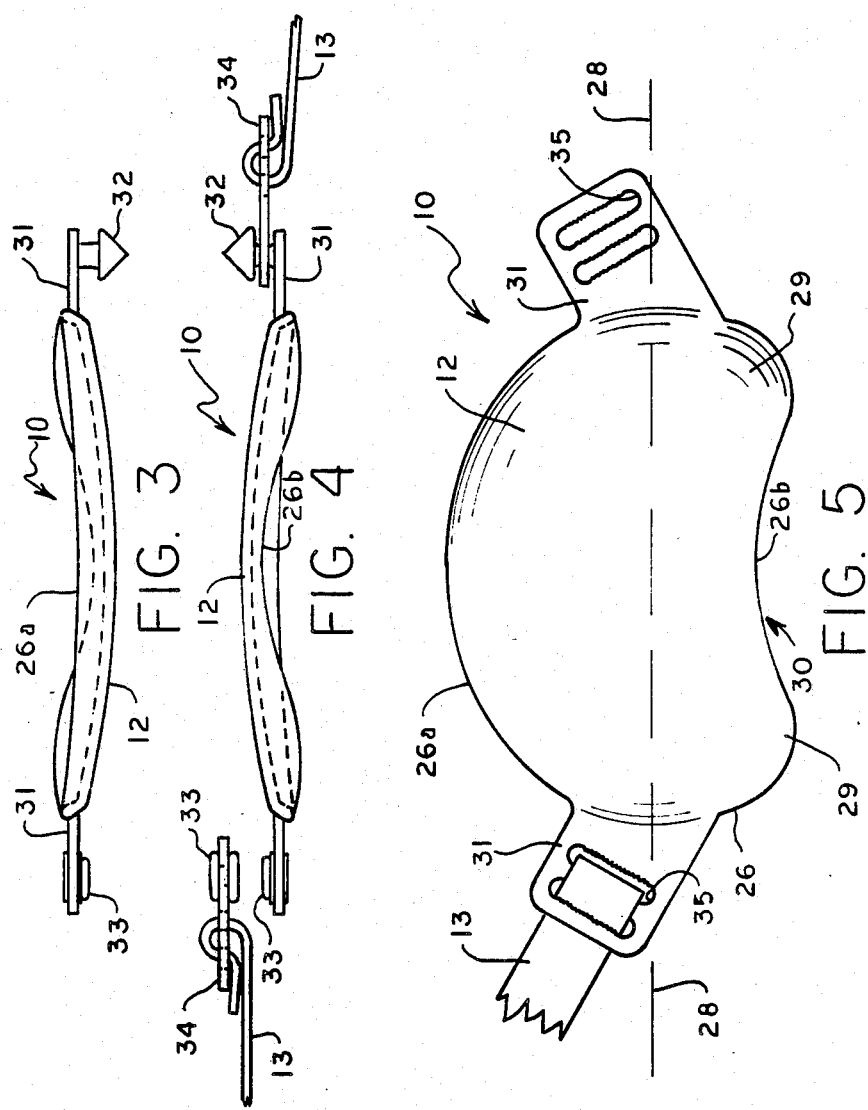

UROSTOMY GUARD

BACKGROUND OF THE INVENTION

1. Field Of The Invention.

The present invention relates to a medical appliance for use by persons who have undergone a urostomy, and more particularly, to an improved guard for shielding an ostomy pouch at the connection of the pouch to the stoma of the ostomy patient.

2. Description Of The Prior Art.

Indivduals who have undergone a permanent urostomy are disposed or required to wear an ostomy pouch. The pouch is attachable to the abdomen of the ostomy patient at the urinary opening, referred to as the stoma, for collection of fluid matter discharged therefrom, thereby allowing the individual to move about unrestrained by remotely connected collection apparatus. Typical ostomy pouches comprise an elongate bag member constructed of a flexible material, such as plastic, and adapted at one end with an annular member, or flange. The flange may be positioned around the stoma and held against the abdomen providing a fluid-tight connection between the pouch and stoma. In one widely used form, the flange of the ostomy bag may be secured to the abdominal skin of the ostomy patient through the use of an adhesive film. The film serves the dual function of supporting the ostomy pouch on the abdomen while providing an environmentally sealed connection to the stoma.

Ostomy pouches of the foregoing type have gained wide acceptance because of their overall convenience in use. Once the flange has been secured to the abdomen of an ostomy patient, it is capable of providing an enviromentally sealed connection to the stoma over extended periods of time. When it is desired that the pouch be emptied, the user may merely unplug the drain at the bottom of the pouch, leaving the flange adhesively secured to the abdomen. However, the adhesive film of typical ostomy pouches is degraded by exposure to water. Thus, should the user wish to shower bathe on a regular basis, the flange will become prematurely detached from the abdomen and require replacement in order to maintain the desired seal around the stoma. As a consequence of frequent changing of the flange, irritation of the peristomal tissue and abdominal skin results.

Additionally, it will be understood that ostomy pouches function merely as container devices and afford little protection of the stoma. Thus with body movement or accidental impact to the abdomen or pouch, the ostomy patient may experience incidents of pain resulting from irritation of the stoma. Accordingly, it is desirable to protect the stoma against such trauma through the use of a relatively rigid guard member. A guard for use in cooperation with an ostomy pouch is disclosed, for example, in U.S. Pat. No. 2,675,002, issued to D. J. Cesare on Apr. 13, 1954. Ostomy guards as heretofore known have had the disadvantages of being inconvenient or uncomfortable to use, or of being too cumbersome to be worn unobtrusively with everyday clothing.

SUMMARY OF THE INVENTION

An object of the invention is to provide an improved guard for use in cooperation with an adhesively secured ostomy pouch.

Another object of the invention is to provide such an improved guard which is capable of forming a water-tight seal with the skin of the ostomy patient upon positioning of the guard over the stoma, thereby protecting the adhesive connection of the ostomy pouch during times when the user is shower bathing.

A further object is to provide such an improved guard which may be comfortably worn when the user is either in a sitting or standing position.

Still a further object is to provide such an improved guard which may be unobtrusively worn with every day clothing.

The present invention is directed to a new and improved guard for use with an ostomy pouch, the pouch having means for forming an environmentally sealed connection with the stoma of an ostomy patient. The guard is configured with a generally concave inner surface and a peripheral edge, a first portion of the edge adapted to form a water-tight seal with the skin of the ostomy patient upon positioning of the guard over the stoma. A second portion of the peripheral edge is turned inwardly toward the center of the guard giving the guard an overall kidney shape. When the guard is in use, such a configuration provides an opening through which the ostomy pouch extends, and also permits the guard to be worn comfortably when the user is either in a sitting or standing position.

BRIEF DESCRIPTION OF THE DRAWINGS

Further objects and advantages and a better understanding of the present invention may be had from reference to the accompanying drawings wherein:

FIG. 3 is a top view of the urostomy guard shown in FIG. 1;

FIG. 4 is a bottom view showing the general arrangement of the attachment means for the urostomy guard of the present invention; and, FIG. 5 is a front elevation of an urostomy guard in accordance with the present invention having alternative means for attachment to the ostomy patient.

DESCRIPTION OF THE PREFERRED EMBODIMENTS

Figure 1:
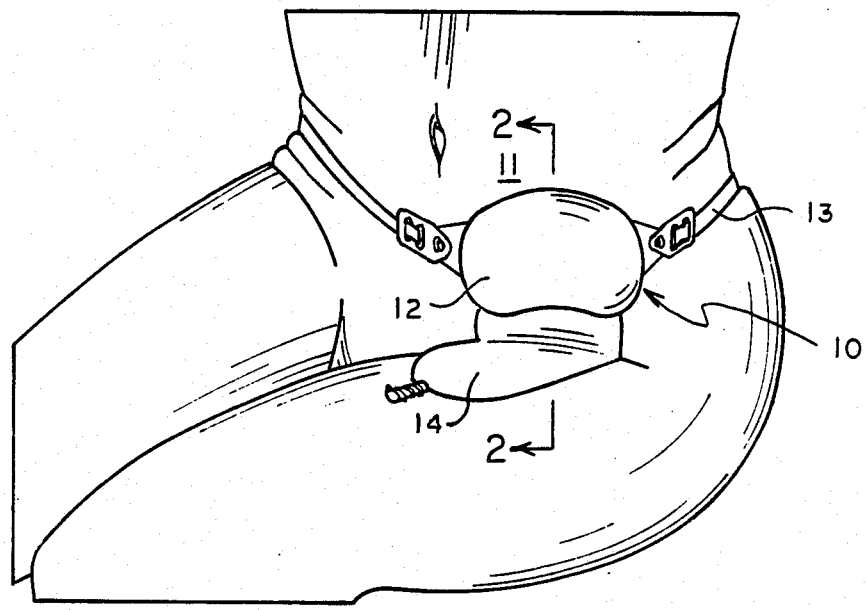
FIG. 1 is a perspective view of an urostomy guard embodying the present invention, illustrated as in use with an ostomy pouch.

Referring now to the drawings, and initially to FIG. 1, an urostomy guard, designated generally by the reference numeral 10 is illustrated as positioned against the abdomen 11 of an ostomy patient and comprises a body member 12 and a belt 13. The belt 13, suitably dimensioned to extend around the torso of the ostomy patient 12 and constructed of a flexible material, serves to comfortably retain the urostomy guard 10 in fixed disposition against the abdomen 11 at the location of the stoma. An ostomy pouch, designated generally by the reference numeral 14, extends downwardly from the underside of the urostomy guard 10, in a manner which will be described in greater detail hereinafter.

Figure 2:
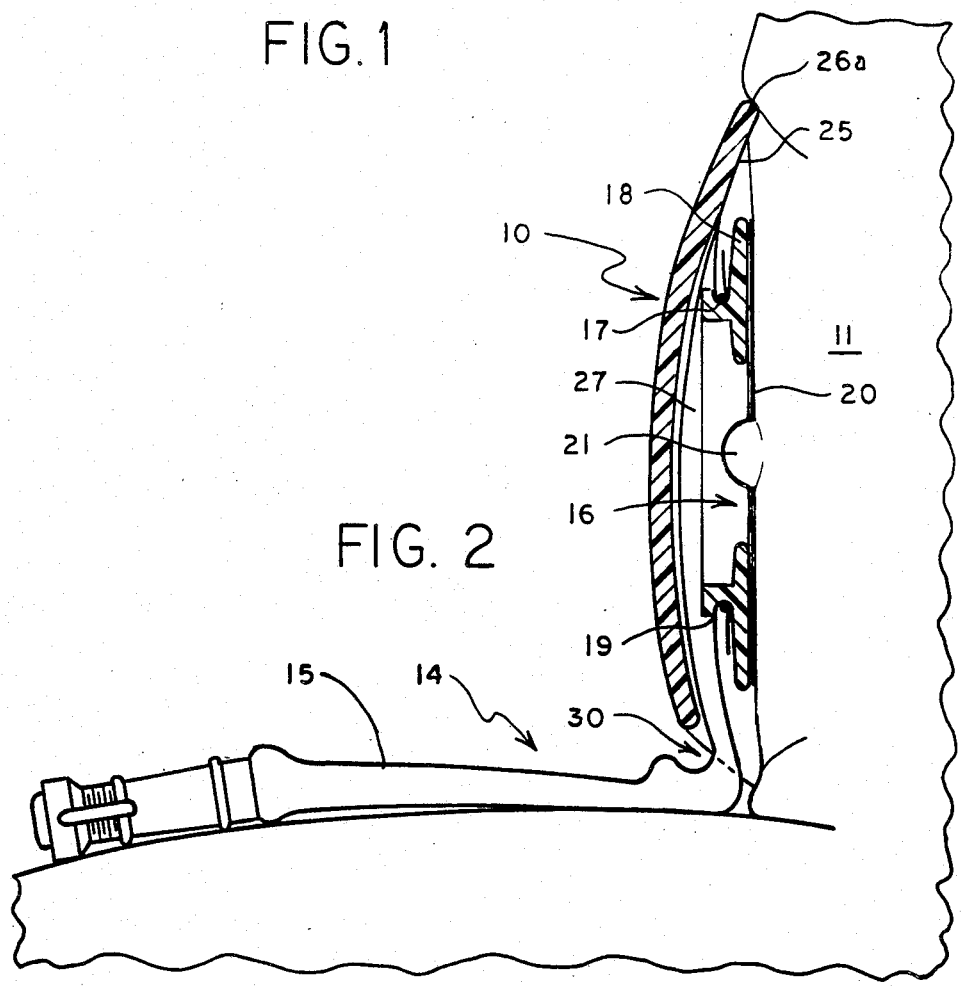
FIG. 2 is a side view, partially in cross-section and on an enlarged scale, of the guard and ostomy pouch shown in FIG. 1.

Turning now to FIG. 2, the ostomy pouch 14 is seen to include an elongate bag 15 which is capable of being folded or bent to conform to the position of the user's body. The bag 15 is formed at one end with an aperture 16 circumscribed by an integrally formed resilient band 17. A flange 18 is provided with an annular groove 19 which receives the resilient band 17 and, thereby, provides a sealed connection between the flange 18 and bag 15. By such an arrangement, the bag 15 may be selectively disconnected from the flange 18, when it is cleaned or replaced, for example.

The ostomy pouch 14 is of a type which may be applied to the ostomy patient without reliance on a belt or straps to hold the pouch 14 in place. To this end, the flange 18 is adapted with an adhesive film 20 for securing the pouch 14 firmly to the abdomen 11. When in use, a portion of the film 20 at the center of the flange 18 is severed to form an aperture such that the flange 18 may be positioned against the abdomen 11 with the stoma 21 of the ostomy patient projecting therethrough. The adhesive film 20 thereby provides an environmentally sealed connection between the ostomy pouch 14 and the stoma 21.

In accordance with the present invention, in order to shield the flange 18, and thus the stoma 21, the body 12 of the guard 10 is configured with a generally concave inner surface 25 defining a peripheral edge 26 projecting generally toward the abdomen 11 of the ostomy patient. The surface 25 is sufficiently concave to allow an upper portion of the edge 26a to form a water-tight seal with the abdominal skin while providing a cavity, designated generally by the reference numeral 27, overlying the flange 18. The surface 25 is preferably spaced from the flange 18 such that restriction of fluid discharges into the ostomy pouch 14 will not result when the guard 10 is in use.

As best seen in FIG. 5, the overall shape of the body 12 of the guard is a curvilinear configuration with its major axis 28 intended to be oriented in a generally horizontal plane when the guard 10 is in use. The body 12 of the guard 10 is substantially symmetrical about a vertical plane extended through the geometric center thereof so that the guard 10 can be used on either side of the abdomen 11 with the same degree of comfort. Above the axis 28, the peripherial edge portion 26a defines a substantially continuous arc. On each side of the body 12, the edge 26 is configured with a decreased radius of curvature such that it turns inwardly defining a pair of lobes 29. Interconnecting the lobes 29 is a lower edge portion 26b having reverse curvature from that of the upper edge portion 26a, thus giving the body 12 an overall kidney-shaped configuration. As best seen in FIG. 2, this configuration together with the concavity of the guard 10 cooperate to define an opening 30 along the underside of the guard 10 when the guard 10 is in use. The opening 30 serves to provide unrestricted exit of the ostomy pouch 14 from beneath the guard 10.

Various means may be employed to secure the guard 10 to the ostomy patient. In a preferred form, and as best illustrated in FIGS. 3 and 4, the guard 10 may be provided with integrally formed laterally extending ears 31, 31 having a lug 32 and snap fastener 33 for connection to respective buckles 34, 34 of a suitable belt 13. By employing a lug and snap fastner arrangement a pivotal connection between the guard 10 and the belt 13 is provided, allowing the guard 10 to assume a proper disposition over the stoma 21 as the belt 13 is extended around the torso of the ostomy patient. Such an arrangement further affords convenience in attaching and removing the urostomy guard 10.

As shown in FIG. 5, ears 31, 31, may be provided, alternatively, with slots 35, 35 for direct connection of the belt 13 to the guard 10. However, in such an arrangement, the ears 31, 31 are preferably disposed at an acute angle with respect to the horizontal axis 28 of the guard 10, projecting in an upward direction such that the belt 13 may conform to the shape of the user's torso while retaining the guard 10 in proper disposition with respect to the stoma 21. In this regard, with the ears 31, 31 angled upwardly, as viewed in FIG. 5, the force of the belt 13 is transmitted to the guard 10 as to apply concentrated pressure along the upper peripheral edge 26a, thereby increasing the sealing capability of the guard 10.

It should be understood from the foregoing description that the guard 10 of the instant invention may be comfortably worn by the ostomy patient while providing protection for both the stoma 21 as well as for the connection between the pouch 14 and abdomen 11. Moreover the novel configuration of the peripheral edge 26 of the guard 10 provides both a water-tight seal along the upper edge 26 of the guard 10 as well as an opening 30 for the ostomy pouch 14 along the lower edge 26a between the lobes 29 of the guard body 12. Moreover, as best illustrated in FIGS. 3 and 4, the guard body 11 may be configured with a curved cross-sectional shape so that the edge 26a more comfortably conforms to the curvature of the torso when the guard 10 is in place over the stoma. The user may, therefore, bathe by showering as often as desired without causing the flange 18 to become prematurely disassociated from the abdomen 11 and requiring that the flange 18 be replaced. In addition, because the peripheral edge 26 defines a kidney-shaped configuration, the user's leg may be raised towards the torso, as in a sitting position, for example, without movement of the guard 10 from its preferred disposition over the stoma 21. Thus, the ostomy patient is free to assume either a sitting or standing position while the guard 10 is in use. Moreover, the water-tight seal between the guard 10 and abdomen 11 is maintained continuously whether the user is in a standing or sitting position.

While only two embodiments of the present invention have been shown, it will be understood that various changes and modifications may occur to those skilled in the art and it is contemplated by the appended claims to cover all such changes and modifications as fall within the true spirit and scope of the present invention.

What is claimed as new and desired to be secured by Letters Patent of the United States is:

1. A guard to protect an ostomy pouch of the type including a collection bag connected to a flange, the flange having means for adhesively securing the pouch to the abdomen of an ostomy patient for receiving discharges from the stoma, comprising a unitary body having a generally concave inner surface and a peripheral edge, the body defining a major plane oriented horizontally when the guard is in use and a minor plane oriented at rights angles thereto, the body being substantially symmetrical about the minor plane, a first portion of said peripheral edge defining an arc lying above said major horizontal plane and a pair of lobes lying below said major plane and further defining a vertical plane passing tangentially to inner surface portions of said lobes, a second portion of said edge defining a second arc curved generally inwardly of said guard toward said major horizontal plane and interconnecting said pair of lobes, said first edge portion configured to define a third arc curving generally outwardly of said vertical plane, whereby when the guard is in use with an ostomy pouch said first portion of said peripheral edge provides a seal with the surface of the abdomen of an ostomy patient, the inner surface of the guard is spaced from the pouch at the connection of the flange to the abdomen and the second portion of the peripheral edge is spaced from the abdomen defining an opening through which a portion of the pouch extends.

2. The guard of claim 1 wherein said peripheral edge defines a generally kidney-shaped configuration.

3. The guard of claim 1 wherein said concave inner surface is spaced from said connection between the pouch and stoma when said fluid-tight seal is formed.

4. The guard of claim 1 comprising belt means for securing the guard in fixed disposition over said stoma.

5. The guard of claim 4 comprising laterally extending ears to which said belt means may be selectively secured.

6. The guard of claim 5 wherein said ears project upwardly at an acute angle with respect to the major axis of the guard whereby said belt applies concentrated pressure along the first portion of said peripheral edge when the guard is in use.

* * * * *